United States Patent
Shiga

(10) Patent No.: US 8,679,812 B2
(45) Date of Patent: Mar. 25, 2014

(54) METHOD FOR EXTRACTING STAPHYLOCOCCUS AUREUS ANTIGEN, REAGENT FOR EXTRACTING STAPHYLOCOCCUS AUREUS ANTIGEN, AND METHOD FOR ASSESSING STAPHYLOCOCCUS AUREUS

(75) Inventor: Kazuki Shiga, Noda (JP)

(73) Assignee: Kikkoman Corporation, Noda-shi, Chiba (JP)

(*) Notice: Subject to any disclaimer, the term of this patent is extended or adjusted under 35 U.S.C. 154(b) by 0 days.

(21) Appl. No.: 13/519,247

(22) PCT Filed: Dec. 22, 2010

(86) PCT No.: PCT/JP2010/073186
§ 371 (c)(1), (2), (4) Date: Jun. 26, 2012

(87) PCT Pub. No.: WO2011/081075
PCT Pub. Date: Jul. 7, 2011

(65) Prior Publication Data
US 2012/0295812 A1 Nov. 22, 2012

(30) Foreign Application Priority Data
Dec. 28, 2009 (JP) .................. 2009-296642

(51) Int. Cl.
C12N 9/10 (2006.01)

(52) U.S. Cl.
USPC .......................................... 435/193; 435/183

(58) Field of Classification Search
None
See application file for complete search history.

(56) References Cited

U.S. PATENT DOCUMENTS

2010/0221747 A1  9/2010  Ito

FOREIGN PATENT DOCUMENTS

| JP | 05-339289 A | 12/1993 |
| JP | 06-054700 A | 3/1994 |
| JP | 07-274993 A | 10/1995 |
| JP | 10-078382 A | 3/1998 |
| JP | 3638731 B2 | 3/1998 |
| WO | WO 2004059280 | * 7/2004 |
| WO | WO 2007/069673 A1 | 6/2007 |

OTHER PUBLICATIONS

W.F. Verwey, "A Type-Specific Antigenic Protein Derived From the Staphylococcus," J. Exp. Med., vol. 71, No. 5, (1940), pp. 635 to 644.
G.K. Hirst et al., "Antigenic Properties of the Type-Specific Substance Derived From Group a Hemolytic Streptococci," J. Exp. Med., vol. 69, No. 3, (1938), pp. 425 to 445.
Denise M. O'Hara et al., "Antibody Used to Identify Penicillin-Binding Protein 2' in Methicillin-Resistant Strains of Staphylococcus aureus," FEBS Lett., vol. 212, No. 2, (1987), pp. 237 to 241.
Julie Louise Gerberding et al., "Comparison of Conventional Susceptibility Tests with Direct Detection of Penicillin-Binding Protein 2a in Borderline Oxacillin-Resistant Strains of Staphylococcus aureus," Antimicrobial Agents and Chemotherapy, vol. 35, No. 12, (1991), pp. 2574 to 2579.
Kiyoshi Sekiguchi et al., "Detection of Methicillin-Resistant Staphylococcus aureus (MRSA) with Antibodies against Synthetic Peptides Derived from Penicillin-Binding Protein 2'," Microbiol. Immunol., vol. 39, No. 8, (1995), pp. 545 to 550.
K. Ubukata et al., Rapid Detection of the mecA Gene in Methicillin-Resistant Staphylococci by Enzymatic Detection of Polymerase Chain Reaction Products, Journal of Clin. Microbiol., vol. 30, No. 7, (1992), pp. 1728 to 1733.
P.A. Mashimo et al., "Selective Recovery of Oral Capnocytophaga spp. with Sheep Blood Agar Containing Bacitracin and Polymyxin B.," Journal of Clin. Microbiol., vol. 17, No. 2, (1983). pp. 187 to 191.

* cited by examiner

Primary Examiner — Padma V Baskar
(74) Attorney, Agent, or Firm — Holtz Holtz Goodman & Chick PC

(57) ABSTRACT

The invention provides a method for extracting a Staphylococcus aureus antigen which comprises using an extraction reagent with a pH of no higher than 5.0, containing one or more acids selected from among hydrochloric acid, acetic acid, citric acid, phosphoric acid, sulfuric acid and nitric acid, to extract a Staphylococcus aureus antigen comprising a methicillin-resistant Staphylococcus aureus antigen and/or a methicillin-sensitive Staphylococcus aureus antigen, from Staphylococcus aureus in a specimen. The invention further provides a method for assessing Staphylococcus aureus.

4 Claims, 2 Drawing Sheets

① PBP2 antibody
② PBP2' antibody
③ Biotinylated BSA

MRSA measurement image

MSSA measurement image

METHOD FOR EXTRACTING *STAPHYLOCOCCUS AUREUS* ANTIGEN, REAGENT FOR EXTRACTING *STAPHYLOCOCCUS AUREUS* ANTIGEN, AND METHOD FOR ASSESSING *STAPHYLOCOCCUS AUREUS*

CROSS-REFERENCE TO RELATED APPLICATION

This application is a United States national phase application of International Application PCT/JP2010/073186 filed Dec 22, 2010.

TECHNICAL FIELD

The invention relates to a method for extracting a *Staphylococcus aureus* antigen, to a reagent for extracting a *Staphylococcus aureus* antigen, and to a method for assessing *Staphylococcus aureus*.

The present application is a patent application relating to the results of national and other sponsored research (patent application submitted under Article 19 of the Industrial Technology Enhancement Act, for Development of Systems and Technology For Advanced Measurement and Analysis by the Japan Science and Technology Agency, 2008, 2009 and 2010).

BACKGROUND ART

*Staphylococcus aureus* (*S. aureus*) is a pathogenic bacterium that causes various diseases in humans and animals. *Staphylococcus aureus* contaminates foods, and upon proliferation produces exotoxins (enterotoxins). When foods containing enterotoxins are consumed, symptoms of acute gastroenteritis appear within 2-6 hours and are followed by vomiting, abdominal pain and diarrhea. In serious cases this is accompanied by lower grade fever, fall in marked symptoms of poisoning including blood pressure, intrathoracic anxiety, clouding of consciousness and pulse rate reduction, often requiring emergency hospital admission.

Methicillin-resistant *Staphylococcus aureus* (hereunder referred to as "MRSA") is a type of *Staphylococcus aureus* causing hospital infections that have come to constitute a serious social problem. In recent years, various multiple drug-resistant MRSA species have appeared that exhibit resistance to many other antibiotics other than methicillin, including β-lactam agents such as penicillin-based and cephem-based antibiotics. Because MRSA has such multiple drug resistance, it is difficult to treat its infection. *Staphylococcus aureus* also includes methicillin-sensitive *Staphylococcus aureus* (hereunder referred to as "MSSA").

While effective methods of treating MRSA have been developed in recent years, from the viewpoint of side-effects and preventing emergence of new resistant strains, it is considered undesirable to employ methods of treating MRSA-infected patients as standard treatment for patients infected with MSSA that does not have multiple drug resistance. That is, it is important to promptly identify MRSA and carry out appropriate measures for MRSA patients or MRSA-infected areas, and when *Staphylococcus aureus* has been detected, it is extremely important to reliably discern whether the strain is MRSA, or MSSA which does not have multiple drug resistance and requires different measures than MRSA, so that appropriate measures may be taken for each.

Conventional assessment of *Staphylococcus aureus* as MRSA or MSSA has been made by methods in which actual resistance to drugs is examined by culturing using a dilution method, disc sensitivity test or the like. However, such methods require long culturing times, and are associated with problems including variable results depending on various factors during culturing (inoculum concentration, culturing temperature, medium composition, drugs used, etc.), as well as the proficiency of the operating technician.

On the other hand, as means for discriminating MRSA/MSSA based on the presence of PBP2', which is a new alternate enzyme for penicillin-binding proteins (PBP1, PBP2, PBP3 and PBP4), the characteristic proteins of MRSA, there have been proposed methods for detecting PBP2' by nonradioactive testing (see Non-patent documents 1 and 2, for example) or radioimmunoassay and enzyme immunoassay methods using antibodies for PBP2' (see Patent document 1 and Non-patent document 3, for example). However, such methods require the complex procedure of preparing an antigen-containing cell membrane fraction by ultracentrifugation, and they are difficult to carry out at ordinary examination facilities. In addition, such methods employ urea as a denaturing agent for extraction of the antigen, and therefore urea remains in the reaction system during subsequent immunoassay so that a measuring time of several hours is necessary, thus posing another inconvenience for routine examination.

There are also known methods for detection of mecA, the gene coding for PBF'2' produced by multiple-drug-resistant *Staphylococcus aureus*, by PCR-based genetic engineering techniques, whereby MRSA is discriminated based on the presence of the gene in the test strain (see Non-patent document 4, for example). However, the presence of mecA does not necessarily reflect multiple drug resistance of *Staphylococcus aureus*, and *Staphylococcus aureus* strains are known to exist that do not acquire multiple drug resistance despite carrying the mecA gene.

On the other hand, methods are known for extracting PBP2' antigen from MRSA without complex procedures such as ultracentrifugation of the cell membrane fraction, and such methods include extraction with alkali metal hydroxides, alkaline earth metal hydroxides or amine aqueous solutions (see Patent document 2, for example).

CITATION LIST

Patent Literature

[Patent document 1] Japanese Unexamined Patent Application Publication HEI No. 5-339289
[Patent document 2] Japanese Patent Publication No. 3638731

Non-Patent Literature

[Non-patent document 1] D. M. O'Hara et al., FEBS Lett. Vol. 212, No. 2, p 237-241,(1987)
[Non-patent document 2] J. L. Gerberding et al., Antimicrobial Agents and Chemotherapy Vol. 35, No. 12, 2574-2579, (1991)
[Non-patent document 3] K. Sekiguchi et al., Microbiol. Immunol. Vol. 39, p 545-550,(1995)
[Non-patent Document 4] Ubukata et al., J. Clin. Microbiol., Vol. 30, p. 1728-1 73341992)
[Non-patent document 5] Gerber, Journal of Clin. Micro., pp. 187-189, (1983)

SUMMARY OF INVENTION

Technical Problem

As mentioned above, detection of *Staphylococcus aureus* cannot be considered sufficient if only MRSA alone is detected, and at the current time it is important to first determine whether or not *Staphylococcus aureus* is detected, and to then distinguish whether or not it is MRSA, or MSSA which does not have multiple drug resistance, and to implement appropriate measures. Considering this, however, much room still exists for improvement in the reliability of detection methods that are based on the idea of extracting only PBP2' by the aforementioned method and detecting it by some means.

Specifically, methods of extracting and detecting only PBP2' allow the cells (specimen) being subjected to detection to be judged as MRSA if PBP2' is detected in the extract of the specimen. However, if PBP2' is not detected, it cannot be judged whether the specimen is MSSA based on that result alone. This is because it may be that PBP2' was not detected due to the fact that the specimen was not MSSA, but it may also be due to various other reasons, such as that the specimen was not *Staphylococcus aureus*, or that it was *Staphylococcus aureus* (MRSA or MSSA) but the amount of specimen provided for the test was too small, or that the test was conducted under improper detection conditions, such as with some procedural error.

In order to confirm that a specimen is MSSA, it is necessary to carry out a procedure of extracting and detecting PBP2' and PBP2, and then confirming whether PBP2 alone is detected without detection of PBP2'. For a specimen in which PBP2' is not detected and PBP2 is also not detected, presumably other strategies are necessary, including re-measurement or redesign of the measurement procedure, and confirmation of the bacterial strain. This is difficult to deal with in methods aimed at detection of PBP2' alone.

Examples of known methods for extraction of antigens from microorganisms include "micronitrous acid extraction" wherein an antigen is extracted from *Streptococcus* microorganisms using nitrous acid (see Non-patent document 5, for example). The present inventors have confirmed, however, that this extraction method is not suited for extraction of antigens, such as extraction of PBP2' and/or PBP2, from *Staphylococcus aureus*.

That is, there are desired an extraction method that allows efficient simultaneous extraction of PBP2' and F'BP2 from *Staphylococcus aureus*, and can keep both in the extract in a measurable form, and an assessment method that can detect the extracted PBP2' and PBP2, and based on the results, can conveniently and more reliably assess whether the *Staphylococcus aureus* strain being assessed is methicillin-resistant or methicillin-sensitive.

It is an object of the invention to provide an extraction method that allows efficient simultaneous extraction of PBP2' and PBP2 from *Staphylococcus aureus*, and can keep both in the extract in a measurable form, as well as an extraction reagent therefor. It is another object of the invention to provide a method for assessing *Staphylococcus aureus* which can more reliably assess whether a specimen is MRSA or MSSA, based on results of detection of antigen in an extract obtained using the aforementioned extraction method and extraction reagent.

Means to Solve Problems

As a result of diligent research. the present inventors have completed this invention upon finding that both antigens can be extracted from *Staphylococcus aureus* using an acidic aqueous solution containing a specific acid, with both antigens being kept in the extract, and that the objects stated above can be achieved by detecting each of the antigens in the extract by an immunoassay method.

That is, according Cu the invention there is provided a method for extracting a *Staphylococcus aureus* antigen which comprises a step of using an extraction reagent with a pH of no higher than 5.0 containing one or more acids selected from among hydrochloric acid, acetic acid, citric acid, phosphoric acid, sulfuric acid and nitric acid, to extract a *Staphylococcus aureus* antigen including a methicillin-resistant *Staphylococcus aureus* antigen and/or a methicillin-sensitive *Staphylococcus aureus* antigen, from *Staphylococcus aureus* in a specimen. According to this method, it is possible to simultaneously and efficiently extract PBP2' and PBP2 from *Staphylococcus aureus*. It is also possible to stably keep PBP2' and PBP2 in the extract.

According to the invention there is also provided a method for assessing *Staphylococcus aureus* which comprises using an extraction reagent with a pH of no higher than 5.0 containing one or more acids selected from among hydrochloric acid, acetic acid, citric acid, phosphoric acid, sulfuric acid and nitric acid, to extract a *Staphylococcus aureus* antigen including a methicillin-resistant *Staphylococcus aureus* antigen and/or a methicillin-sensitive *Staphylococcus aureus* antigen, from *Staphylococcus aureus* in a specimen; detecting the extracted *Staphylococcus aureus* antigen by an immunoassay method using antibody for the *Staphylococcus aureus* antigen, and assessing whether the *Staphylococcus aureus* in the specimen is methicillin-resistant *Staphylococcus aureus* or methicillin-sensitive *Staphylococcus aureus* based on the results of the detection. According to this method it is possible to more reliably assess whether a specimen is MRSA or MSSA, based on results of detection of antigen in the obtained extract.

According to the invention there is also provided a reagent for extraction of a *Staphylococcus aureus* antigen, comprising one or more selected from among hydrochloric acid, acetic acid, citric acid, phosphoric acid, sulfuric acid and nitric acid, and having a pH of no higher than 5.0. With such a reagent it is possible to simultaneously and efficiently extract PBP2' and PBP2 from *Staphylococcus aureus*, and to stably keep PBP2 and PBP2 in the extract.

According to the invention there is further provided an immunoassay kit for detection of *Staphylococcus aureus*, comprising the aforementioned reagent for extraction of *Staphylococcus aureus* antigen. With such a kit it is possible to more reliably assess whether a specimen is MRSA or MSSA, based on results of detection of antigen in the obtained extract.

Advantageous Effects of Invention

According to the invention it is possible to simultaneously and efficiently extract PBP2' and PBP2 from *Staphylococcus aureus*, and to stably keep PBP2' and PBP2 in the extract. According to the invention it is also possible to more reliably assess whether a specimen is MRSA or MSSA, based on results of detection of antigen in the obtained extract.

DESCRIPTION OF EMBODIMENTS

Figure 1:
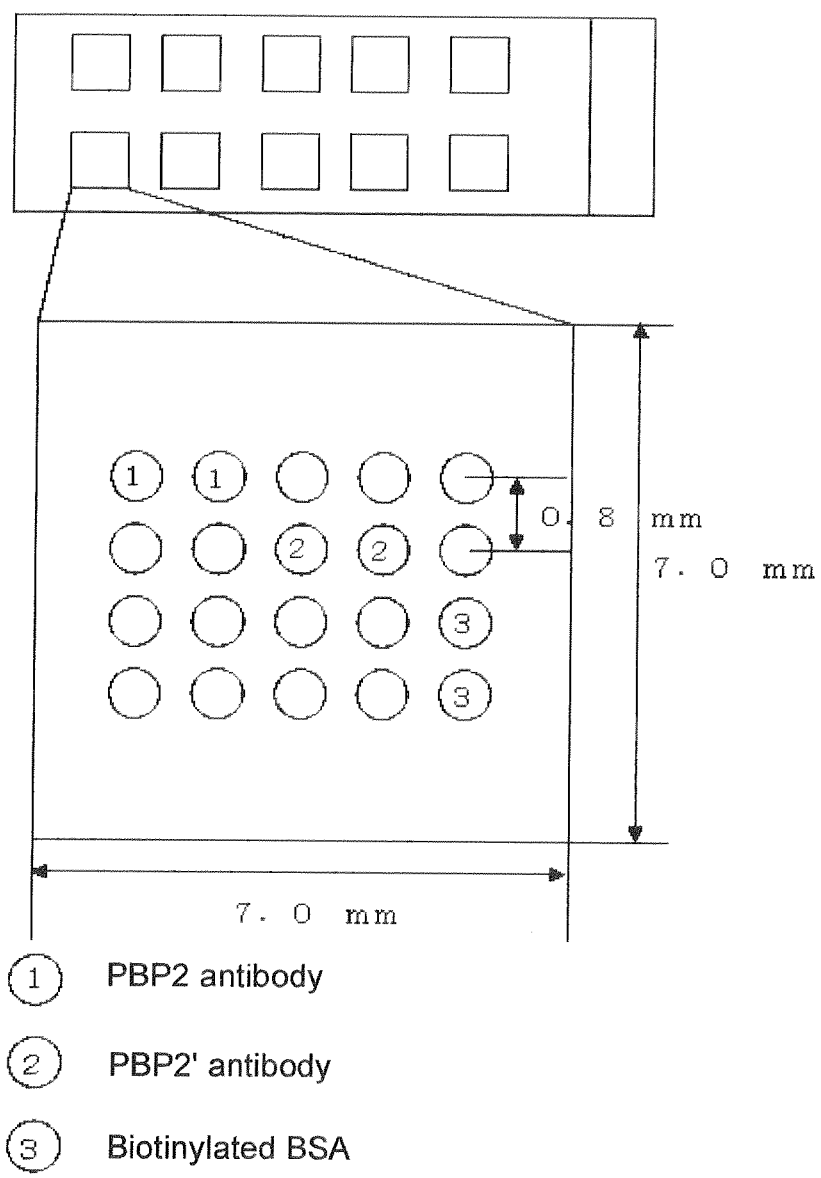
FIG. 1 is a design drawing of a prepared antibody array.

[Explanation of Terms]
As used herein, the term "*Staphylococcus aureus*" refers to *Staphylococcus* which are resident flora (enterobacteria) in the human and animal skin and gastrointestinal tract (bowel). It is also a cause of various epidermal infectious disease in humans such as abscess, of food poisoning, and of fatal infectious disease including pneumonia, cerebrospinal meningitis and sepsis.

As used herein, the term "methicillin-resistant *Staphylococcus aureus* (MRSA)" refers to *Staphylococcus aureus* that has acquired drug resistance to the antibiotic methicillin, and it also includes MRSA with multiple drug resistant MRSA exhibiting resistance to many antibiotics other than methicillin, including penicillin-based and cephem-based antibiotics as β-lactam antibiotics. On the other hand, the term "methicillin-sensitive *Staphylococcus aureus* (MSSA)", as used herein, refers to *Staphylococcus aureus* that is sensitive to methicillin.

The term "PBP2' (penicillin-binding protein 2')", as used herein, refers to a peptidoglycan synthase which is a different crosslinking enzyme than the 4 cell wall synthases naturally present in *Staphylococcus aureus*, i.e. the penicillin-binding proteins: PBP1, PBP2, PBP3 and PBP4, and it is a characteristic protein of MRSA. That is, MRSA has PBP2' while MSSA does not have PBP2'. Incidentally, both MRSA and MSSA have the 4 penicillin-binding proteins: PBP1, PBP2, PBP3 and PBP4.

As used herein, the term "*Staphylococcus aureus* antigens" is used to include both methicillin-resistant *Staphylococcus aureus* antigens and methicillin-sensitive *Staphylococcus aureus* antigens, and specifically, it includes protein PBP2' which is characteristic of methicillin-resistant *Staphylococcus aureus*, in addition to the 4 penicillin-binding proteins: PBP1, PBP2, PBP3 and PBP4 naturally present in *Staphylococcus aureus*, and preferably includes PBP2 and PBP2'. Also, the term "methicillin-resistant *Staphylococcus aureus* antigen" as used herein referrs to penicillin-binding protein 2' (PBP2'). The term "methicillin-sensitive *Staphylococcus aureus* antigen" as used herein refers to a *Staphylococcus aureus* antigen other than PBP2', and preferably PBP2.

Embodiments of the invention will now be explained in detail.

[Embodiment 1: Method for Extracting *Staphylococcus aureus* Antigen]

The method for extracting a *Staphylococcus aureus* antigen according to this embodiment is a method for extracting *Staphylococcus aureus* antigen which comprises: using an extraction reagent with a pH of no higher than 5.0 containing one or more acids selected from among hydrochloric acid, acetic acid, citric acid, phosphoric acid, sulfuric acid and nitric acid, to extract a *Staphylococcus aureus* antigen including a methicillin-resistant *Staphylococcus aureus* antigen and/or a methicillin-sensitive *Staphylococcus aureus* antigen, from *Staphylococcus aureus* in a specimen.

(Acid in Extraction Reagent)

The extraction reagent that may be used in the extraction method of this embodiment contains one or more acids selected from among hydrochloric acid, acetic acid, citric acid. phosphoric acid, sulfuric acid and nitric acid. Using such acids will allow the object of the invention to be satisfactorily achieved.

(pH of Extraction Reagent)

The extraction reagent that may be used for the extraction method of this embodiment has a pH of no higher than 5.0. The pH of the extraction reagent is not particularly restricted so long as it is no higher than 5.0, but it is more preferably no higher than 4.5 and even more preferably no higher than 4.0. In addition, the extraction reagent of this embodiment is preferably adjusted to have a pH of no higher than 5.0 during extraction. For example, when the sample is a cell suspension of MRSA, the pH is preferably no higher than 5.0 when the cell suspension is mixed with the extraction reagent of the invention. The concentration of the acid in the extraction reagent is preferably 0.05 M to 0.5 M.

(Surfactant in Extraction Reagent)

Various surfactants may be optionally added to an extraction reagent that may be used in the extraction method of this embodiment. This will allow more efficient extraction of PBP2' and PBP2 from *Staphylococcus aureus*. The surfactant used may be any one selected from among anionic surfactants, cationic surfactants, nonionic surfactants and zwitterionic surfactants.

Examples of anionic surfactants include carboxylic acid salt and sulfonic acid salt types (for example, alkylbenzene carboxylates, alkylbenzene sulfonates, alkyl sulfonates, sulfosuccinate esters and the like), sulfuric acid ester salt types (for example, alkyl sulfate ester salts, polyoxyalkylene alkyl ether sulfate ester salts or polyoxyethylene lauryl ether sulfate ester salts), and phosphoric acid ester salt types (for example, alkyl phosphate ester salts, polyoxyalkylene alkyl ether phosphate ester salts or polyoxyalkylene alkylaryl ether phosphate ester salts). These may be commercially available products, and for example, sodium polyoxyethylene lauryl ether sulfate is marketed under the trade name of EMAL® 20C (Kao Corp.). and sodium polyoxyethylene nonylphenyl ether sulfate is marketed under the trade name of EMAL® NC-35 (Kao Corp.).

Cationic surfactants include alkylamine salt types (for example, monomethylamine hydrochloride, dimethylamine hydrochloride and trimethylamine hydrochloride, and quaternary ammonium salt types (for example, dodecyltrimethylammonium chloride, hexadecyltrimethylammonium bromide, hexadecylpyridinium bromide, benzyltriethylammonium chloride, didodecyldimethylammonium bromide, benzyldimethylphenylammonium chloride, tetrahexylammonium chloride, stearyldimethylbenzylammonium chloride, stearyltrimethylammonium chloride and lauryltrimethylammonium chloride). These may be commercially available products, and for example, stearyltrimethylammonium chloride is marketed under the trade name of QUARTAMIN® 86W (Kao Corp.), and lauryltrimethylammonium chloride is marketed under the trade name of QUARTAMIN® 24P (Kao Corp.).

Nonionic surfactants include ether types (for example, polyoxyethylenealkyl ethers, pentaethylencglycol monododecyl ether, octaethyleneglycol monododecyl ether, polyoxyethylene alkylphenyl ethers and polyoxyethylene isooctylphenyl ether), ester types (glycerin laurate, glycerin monostearate, sorbitan fatty acid esters, sucrose fatty acid esters and the like), ester/ether types (polyoxyethylene sorbitan fatty acid ester, polyoxyethylene hexitan fatty acid ester and sorbitan fatty acid ester-polyethylene glycol), alkanolamide types (diethanolamide laurate, diethanolamide oleate and diethanolamide stearate), alkyl glycoside types (octyl glucoside, decyl glucoside and lauryl glucoside) and glucamide types (octanoyl-N-methyl-glucamide, nonanoyl-N-methyl-glucamide and decanoyl-N-methyl-glucamide). These may be commercially available products, and for example, polyoxyethylene(20) sorbitan monolaurate is marketed under the trade name of Tween20, polyoxyethylene octylphenyl ether is marketed under the trade name of Triton™ X-100, and octanoyl-N-methyl-glucamide is marketed under the trade name of MEGA-8. Examples of preferred surfactants include polyoxyethylene isooctylphenyl ethers (for example, TritonX-100), polyoxyethylene nonylphenyl ethers (for example, NP40), polyoxyethylene sorbitol esters (for example, Tween80), polyoxyethylene dodecyl ethers (for example, Brij® 58), polyoxyethylene stearvl ethers (for example, Brij® 721) and octyl glucoside. In addition to these, preferred examples include polyoxyethylene sorbitan monooleate (RHEODOL TW-0120, product of Kao Corp.), a 9-molar adduct of isotridecyl alcohol ethoxylate (LEOCOL TD-90, product of Lion Corp.), and a compound obtained by addition of polypropylene oxide and polyethylene oxide to a higher alkyl group (for example, a C12-14 alkyl group) (LEOCOL SC70, product of Lion Corp.).

Zwitterionic surfactants include sulfonic acid types such as alkyl betaine types (lauryldimethylaminobetaine acetate, stearyldimethylaminobetaine acetate, dodecylaminomethyldimethylsulfopropyl betaine, octadecylaminomethyldimethylsulfopropyl betaine), CHAPS (3-[3-cholamidopropyl]dimethylammonio)-1-propanesulfonic acid) and CHAPSO (3-[cholamidopropyl]dimethylammonio)-2-hydroxy-1-propanesulfonic acid), and amine oxide types (lauryldimethylamine N-oxide and oleyldimethylamine N-oxide). These may be commercially available products, and for example, alkyl betaine types are marketed under the trade name of AMPHITOL® 24B (product of Kao Corp.), and amine oxide types are marketed under the trade name of AMPHITOL® 20N (product of Kao Corp.).

Of the surfactants mentioned above, the preferred examples of surfactants are EMAL® NC35, MEGA-8, TritonX-100 and Tween20, LEOCOL SC70, LEOCOL TD90, RHEODOL TW-0120, Brij® 721, QUARTAMIN® 86W, QUARTAMIN® 24P, CHAPS, CHAPSO, AMPHITOL® 20N and AMPHITOL® 24B. This will allow more efficient extraction of PBP2' and PBP2 from *Staphylococcus aureus*.

The concentration of the surfactant in the extraction reagent of the invention will normally be 0.01% (w/w) or greater, preferably 0.01-5% (w/w), more preferably 0.05-5.0% (w/w), even more preferably 0.05-1.0% (w/w) and yet more preferably 0.1-1.0% (w/w). Sufficient extraction efficiency is obtained if the surfactant concentration is at least 0.01% (w/w). Also, limiting the surfactant concentration to no greater than 5.0% (w/w) is economical since no further improvement in extraction efficiency is seen when the concentration is increased beyond this limit, and is preferred to avoid causing problems such as increased complexity of the procedure due to removal or dilution of the surfactant so that the surfactant does not adversely affect the subsequent measuring system.

The surfactant may be used either alone or as a combination of different types, so long as the intended effect of the invention is not impaired.

The extraction reagent of the invention may also contain other preservatives, buffering agents and the like, so long as the intended effect of the invention is not impaired.

(*Staphylococcus aureus* Antigen Extraction Conditions)

In the method forextracting a *Staphylococcus aureus* antigen according to this embodiment, a *Staphylococcus aureus* antigen is extracted from *Staphylococcus aureus* in a specimen using the aforementioned extraction reagent. The extraction conditions for the extraction method of the invention are not particularly restricted so long as they are suitable conditions for extraction of the *Staphylococcus aureus* antigen, and they may be set to a suitable temperature and extraction time that allow the antigen to be satisfactorily extracted. The antigen extraction temperature is preferably room temperature or higher, and specifically 25-100° C. This will allow more efficient extraction of PBP2' and PBP2 from *Staphylococcus aureus*. The antigen extraction time is preferably between about 1 minute to 60 minutes, and may be optionally longer.

A higher extraction temperature will shorten the time required for extraction, and with extraction at 100° C., for example. the extraction time may be about 1 to 3 minutes, with extraction at 95° C. the extraction time may be about 5 to 10 minutes, and with extraction at about 25-37° C. the extraction time may be about 60 minutes.

According to the extraction method of this embodiment it is possible to efficiently extract antigens from both MRSA and MSSA. It is also advantageous in that both of the extracted antigens are not easily decomposed in the extract, and thus PBP2' and PBP2 can be stably kept in the extract.

[Embodiment 2: Method for Assessing *Staphylococcus aureus*]

The method for assessing *Staphylococcus aureus* according to this embodiment is a method for assessing *Staphylococcus aureus* which comprises: using an extraction reagent with a pH of no higher than 5.0 containing one or more acids selected from among hydrochloric acid, acetic acid, citric acid, phosphoric acid, sulfuric acid and nitric acid, to extract a *Staphylococcus aureus* antigen including a methicillin-resistant *Staphylococcus aureus* antigen and/or a methicillin-sensitive *Staphylococcus aureus* antigen, from *Staphylococcus aureus* in a specimen; detecting the extracted *Staphylococcus aureus* antigen by an immunoassay method using antibody for the *Staphylococcus aureus* antigen; and assessing whether the *Staphylococcus aureus* in the specimen is methicillin-resistant *Staphylococcus aureus* or methicillin-sensitive *Staphylococcus aureus* based on the results of the detection. According to this method it is possible to efficiently detect both PBP2', which is an antigen characteristic of MRSA, and PBP2 which is present in both MRSA and MSSA, while also allowing both to be stably kept in an extract so that both can be detected in an immunoassay at a later stage and reliable assessment can be made as to whether the detected cells (specimen) are MRSA or MSSA.

(Step of Extracting *Staphylococcus aureus* Antigen)

The step of extracting the *Staphylococcus aureus* antigen according to this embodiment basically has the same construction and effect as the method of extracting a *Staphylococcus aureus* antigen according to embodiment 1 described above, and therefore explanation of the same aspects with embodiment 1 will be omitted for convenience.

(Stability of Extracted Antigen in Extraction Reagent)

The step of extracting a *Staphylococcus aureus* antigen from *Staphylococcus aureus* using an extraction reagent according to this embodiment allows antigens to be efficiently extracted from both MRSA and MSSA, while the extracted antiens are both resistant to decomposition in the extract. Since the extraction is carried out for detection of *Staphylococcus aureus* antigen by an immunoassay method in a subsequent step, immediate decomposition of the extracted antigens in the extract interferes with the detection, and makes it impossible to make accurate assessment of MRSA/MSSA. The extraction step of this embodiment is advantageous because the extracted antigen can be stably present without being decomposed in the extraction reagent.

When the extracted *Staphylococcus aureus* antigen is supplied for immunoassay, the extract of the *Staphylococcus aureus* that had been extracted using the extraction reagent of the invention is preferably neutralized as necessary using an appropriate buffering agent or base, and preferably dipotassium hydrogenphosphate, disodium hydrogenphosphate, sodium hydroxide or the like, to adjust the immunoassay system to suitable pH conditions, and specifically pH 6.0-8.0.

Also, after the extraction reagent of the invention has been used to extract an antigen from *Staphylococcus aureus*, the cell debris or granules, or other insolubles, are preferably removed by some method. Their removal may be accomplished, for example, by centrifugal separation, filtration or the like.

(Detection of Extracted *Staphylococcus aureus* Antigen)

In this embodiment, extracted *Staphylococcus aureus* antigen was detected by an immunoassay method using antibody for the *Staphylococcus aureus* antigen. The term "antibody", in this embodiment, refers to any protein generally classified among "antibodies" that recognize various molecules including specific peptides. polysaccharides or low molecular compounds, and that form bonds or crosslinks, and it includes altered and modified forms thereof. Many different types are known, derived from mice, rabbits, sheep and the like, and specific monoclonal antibodies can be produced by cultured cells, or can be produced with *E. coli* or eukaryotic cells using gene recombinant techniques, and such recombinant forms are also included. Fragments of the aforementioned antibodies are also within the scope of the invention. Antibody fragments include F(ab')2 fragments and Fab' fragments. When the antibody is a monoclonal antibody, the globulin type is not particularly restricted and may be, for example, IgG, IgM, IgA, IgE, IgD or the like. The monoclonal antibody may also be a humanized antibody.

Anti-902 antibody and anti-PBP2' antibody may be used as antibodies for *Staphylococcus aureus* antigens, and these may be polyclonal antibodies or monoclonal antibodies but are preferably monoclonal antibodies. Anti-PBP2 antibody specifically recognizes PBP2. Anti-PBP2' antibody specifically recognizes PBP2'. Anti-PBP2 antibody and anti-PBP2' antibody can be prepared by methods known in the field, and for example, they may be prepared by the method described in Japanese Patent Publication No. 3638731. A commercially available antibody may also be obtained.

The immunoassay method used may be a known immunoassay method, and for example, common immunoassay methods such as latex agglutination methods, turbidimetric methods, radioimmunoassay methods (for example, RIA and RIMA), enzyme immunoassay methods (for example, ELISA and EIA), gel precipitation reaction, flow cytometry, Western blotting, dot blot methods, fluorescent antibody methods (for example, FIA and IFMA), immunochromatography methods and antibody array methods may be mentioned, with no limitation to these. These immunoassay methods are themselves known in the field, and can be easily carried out by a person skilled in the art. The details regarding common teclmical means may be obtained by reference to known reviews and texts.

For detection of an antibody in the immunoassay method of this embodiment, there may be used a labeled antibody comprising a labeling substance capable of generating a signal, and the antibody itself. Instead of direct binding, the antibody and labeling substance may be bound with an avidin-biotin or streptavidin-biotin system, or by a secondary antibody, and this is also within the technical scope of the invention. The secondary antibody used here may be an antibody capable of binding with the primary antibody.

When an enzyme is to be used as the label, peroxidase, microperoxidase, horseradish peroxidase (HRP), alkaline phosphatase, glucose oxidase, β-galactosidase, glucoamylase, carbonic anhydrase, acetylcholine esterase, luciferase, malonic acid ester dehydrogenase, glucose-6-phosphoric acid dehydrogenase or the like may be used as the label. The method of labeling with these enzymes may be a method of oxidizing the sugar chains of the enzyme with periodic acid and bonding the amino acids of an antibody or lectin with the generated aldehyde groups, or a method of introducing maleimide groups or pyridyl sulfide groups into the enzyme and bonding them with the thiol groups in the Fab' fragment for the antibody or lectin.

When an enzyme is to be used as the label, the test sample is incubated with the labeled antibody, and then the free labeled antibody is rinsed off and removed after which the substrate of the labeled enzyme is allowed to act therewith, and the reaction is measured by coloration or the like to detect the labeled antibody. For example, for labeling with peroxidase, hydrogen peroxide is used as the substrate, and is combined with diaminobenzidine or O-phenylenediamine as the coloring reagent to produce brown or yellow color. For labeling with glucose oxidase, 2,2'-azino-di-(3-ethylbenzothiazoline-6-sulfonic acid (ABTS) or the like may be used as the substrate.

When a fluorescent dye is to be used as the label, an antibody may be labeled with a fluorescent dye such as FITC (fluorescein isothiocyanate) or TRITC (tetramethylrhodamine B isothiocyanate), for example. Bonding of the antibody and fluorescent dye may be carried out by a common method.

When a colored labeling substance is to be used as the label, a colloidal metal, colored latex or the like may be used as the label. Typical examples of colloidal metals include metal colloid particles which are dispersed particles such as gold sol, silver sol, selenium sol. tellurium sol or platinum sol. The sizes of the colloidal metal particles are usually preferred to be about 3-60 nm diameter. Typical examples of colored latexes include synthetic latexes such as polystyrene latexes colored with coloring agents such as red and blue agents. A natural latex such as natural rubber latex may also be used as the latex. The size of the colored latex may be selected from among a diameter of about several tens of nm to several hundred nm. These coloring labeling substances may be commercial products, but they may also be processed further or produced by known methods.

Bonding of the antibody and coloring labeling substance may be carried out by a common method. For example, when the coloring labeling substance consists of gold colloid particles which are dispersed gold sol particles, usually the antibody and gold sol are mixed at room temperature to allow physical bonding between them.

The labeling may alternatively employ radioactive isotope labeling (for example, $^{125}$I, $^{131}$I, $^{3}$H, $^{14}$C or the like), and this is also within the scope of the invention.

(ELISA)

Enzyme immunoassay (ELISA) may be used as the immunoassay method for this embodiment. Here, "enzyme immunoassay" (ELISA) is a method of quantitative detection of an antigen for an antibody using an enzyme-labeled antibody, and it is widely used in clinical tests for its excellent quantitation, convenience and reliability (reproducibility). Enzyme immunoassay is a well-known technique, and the details regarding the common technical means are described in known reviews and texts. Several enzyme immunoassay methods are known, among which a method of binding an antigen to an antibody-immobilized plate and detecting the bound antigen with a separate antibody, known as sandwich ELISA, is most widely employed.

The solid phase carrier in sandwich ELISA may be glass, polystyrene, polypropylene, polyethylene, dextran, nylon, amylase, natural or modified cellulose, polyacrylamide, gabbro or magnetite. The material of the solid phase carrier may have a border with any possible structure, so long as the antibody can bind to it. For example, it may consist of spheres such as beads, or it may be circular cylindrical such as the inner surface of a test tube or microtiter plate well. The surface may be flat, for example as a sheet, film, test strip, chip or slide. Preferred supports are nitrocellulose membranes, nitrocellulose-coated slides. 96-well microtiter plates and polystyrene or carboxyl beads. A person skilled in the art will recognize that numerous other supports are suitable for binding of antibodies or antigens, and can confirm such by routine experimentation.

The enzyme immunoassay (ELISA) is not limited only to ELISA using an enzyme as the label, and includes modified methods such as radioimmunoassay (RIA) using a radioactive isotope as the label or fluoroimmunoassay (FIA) using a fluorescent substance as the label. When these individual immunochemical measuring methods are to be applied, they do not require any special conditions or procedures to be set, and reference may be made to known reviews and texts.

The immunoassay method used for this embodiment may be ELISA, and particularly sandwich ELISA.

(Immunochromatography Method)

The immunoassay method used in this embodiment may also be an immunochromatography method. Immunochromatography is a measuring method in which an immune complex is formed by antigen in a specimen, a labeled antibody and a capture antibody when the specimen migrates on a membrane by capillary movement, and buildup of the labeled form can be visually confirmed. This allows convenient measurement since no special apparatus is necessary and no rinsing procedure is required. Immunochromatography is a well-known technique, and the details regarding the common technical means are described in known reviews and texts.

Immunochromatography generally makes use of a capture reagent site and a labeling reagent site. The antibody which is to capture the antigen is immobilized at the capture reagent site. There are no particular limitations on the material of the solid phase carrier used at the capture reagent site, so long as it is an inert material composed of a microporous substance exhibiting capillary action, which does not react with the first reagent, labeling reagent and substance to be detected. Specifically, it may be a fibrous or nonwoven fibrous matrix or a film, composed of polyurethane, polyester, polyethylene, polyvinyl chloride, polyvinylidene fluoride, nylon or nitrocellulose, or a cellulose derivative such as cellulose acetate, or, filter paper, glass fiber filter paper, cloth, cotton or the like. Preferred are cellulose derivative or nylon membranes, filter paper and glass fiber filter paper, and more preferred are nitrocellulose membranes, membranes of mixed nitrocellulose esters (mixtures of nitrocellulose and cellulose acetate), nylon membranes and filter paper.

The concentration for the solid phase of the antibody is preferably 0.1 µg/ml to 10 mg/ml and more preferably 10 µg/ml to 1 mg/ml.

An antibody labeled for detection of an antigen is included at the labeling reagent site. The labeling used may employ appropriate labeling means as described above.

An immunochromatograph is assembled by combining these two sites with a glass filter for supply of specimen, or absorbing filter paper, or the like. The form and size of the medium used is not particularly restricted, and may be such as appropriate for the actual procedure and for observation of the results. For procedural convenience, a support made of plastic or the like may be provided on the back side of the chromatograph medium which has the assessment site formed on the front side. There are no particular restrictions on the properties of such a support, but when the measurement results are to be observed visually, the support preferably has a color shade different from the color shade produced by the labeling substance. and for most purposes it is preferably colorless or white.

(Antibody Array)

The immunoassay method used in this embodiment may employ an antibody array. An antibody array is a method of immobilizing several antibodies on a support and detecting reaction therewith (binding of low molecular compounds or other proteins). By using such an antibody array it is possible to simultaneously evaluate multiple antigens or proteins that include the PBP2 and PBP2' antigens of the invention, thereby allowing rapid detection to be accomplished.

The support of the antibody array is not particularly restricted so long as it is a support commonly used in the relevant field, and for example, it may be a membrane (for example, a nitrocellulose membrane, nylon membrane or PVDF (polyvinylidene fluoride) membrane), glass (for example, a glass slide), plastic, chip, pin, filter, beads, paper, film, fiber bundle, gel, metal (for example, a gold foil), ceramic or the like, with no particular restriction to these. A membrane of nylon, nitrocellulose or PVDF (polyvinylidene fluoride) is suitable as a support for the array of the invention.

Detection of antigen by an antibody array will differ depending on the form of the antibody array used, and for example, it may be accomplished by labeling antigen extracted from a sample and then reacting it with different antibodies on the antibody array, or by using a solid-phase antibody and a labeled antibody for sandwich assay. The labeling used may employ appropriate labeling means as described above.

Theantibody array may be prepared by immobilizing an antibody on a support by a method known in the relevant field. The method of immobilizing the antibody on the support may be, for example, a method of immobilization by covalent bonding, a method of immobilization by noncovalent interaction (for example, ionic bonding, hydrophobic interaction, hydrogen bonding, Van der Waals force or dipole-dipole bonding), or a method of immobilization by electrostatic bonding, but it is preferably a method of immobilization by covalent bond from the viewpoint of experimental reproducibility. When the support is glass, plastic, a gold foil or the like, the functional groups of the amino acids in the antibody react and bond with the functional groups on the support surface, thereby allowing the antibody to be immobilized on the support.

The antibody array of this embodiment can be prepared using any desired method employed for production of protein or nucleic acid arrays. For example, the antibody may be spotted on the array using a split pin, or a microspotter which is a robot printer comprising an ink jet printer. The spotted antibody concentration is preferably 0.1 µg/ml to 10 mg/ml and more preferably 10 µg/ml to 1 mg/ml. The spot size is preferably a radius of between 0.01 mm and 10 mm, and more preferably a radius of between 0.05 mm and 2 mm. An example of a method for producing an antibody array is described in Japanese Patent Public Inspection No. 2010-533842.

When an enzyme that reacts with the substrate and emits light is to be used as the labeling substance, detection with the antibody array may be accomplished, for example, by imaging the entire array region with a CCD (Charge Coupled Devices) camera and performing photometric measurement with the luminescence as the brightness value. The measuring apparatus of the antibody array may be a LAS300 Lumino Image Analyzer (product of FujiFilm Corporation).

The reaction conditions for the antigen-antibody reaction and detection step, and the reagent components used in the reaction, may be optimized in a range that accomplishes the object of the invention. Detection of both the PBP2 and PBP2' antigens according to the invention may be accomplished separately, successively or simultaneously. For example, if a detection system is selected which employs multiple antibodies simultaneously, such as in an immunochromatography method or antibody array, and allows the presence of each antigen to be simultaneously detected, the detection procedure can be further simplified and more efficient detection and assessment can be made.

(Assessment of MRSA/MSSA Using Extract)

In the method for assessing *Staphylococcus aureus* according to this embodiment, it is assessed whether or not *Staphylococcus aureus* in a specimen is methicillin-resistant *Staphylococcus aureus* or methicillin-sensitive *Staphylococcus aureus*, based on detection results obtained after the extraction step and detection step described above.

After performing the step of detecting PBP2' and PBP2 using the different antigen detection methods described above, specimens in which PBP2' was detected in the extract are assessed to be "MRSA". Specimens in which PBP2 was detected but PBP2' was not detected are assessed to be "MSSA".

On the other hand. regarding a specimen in which PBP2' was not detected and PBP2 was also not detected, it may not be a *Staphylococcus aureus* strain, or it may be *Staphylococcus aureus* (MRSA or MSSA) but the amount of specimen provided for the test may have been too small, or the test may have been conducted under improper detection conditions, such as with some procedural error. The method of the invention has more excellent reliability than methods of detecting PBP2' alone, because in such cases it is possible to immediately conduct re-measurement or to redesign the measurement procedure.

[Embodiment 3: Reagent for Extraction of *Staphylococcus aureus* Antigen]

The reagent for extraction of the *Staphylococcus aureus* antigen according to this embodiment is a reagent for detection of *Staphylococcus aureus* antigen comprising one or more acids selected from among hydrochloric acid, acetic acid, citric acid, phosphoric acid, sulfuric acid and nitric acid, and having a pH of no higher than 5.0. According to this reagent, it is possible to simultaneously and efficiently extract PBP2' and PBP2 from *Staphylococcus aureus*.

The reagent for extraction of *Staphylococcus aureus* antigen according to this embodiment basically has the same construction and effect as the extraction reagent described in detail for embodiment 1. Explanation of the aspects similar to embodiment 1 will therefore be omitted as appropriate. The reagent for extraction of a *Staphylococcus aureus* antigen according to this embodiment may be prepared by combining the components mentioned above. In addition, the reagent for extraction of a *Staphylococcus aureus* antigen according to this embodiment may contain one or more surfactants selected from among anionic surfactants, nonionic surfactants, cationic surfactants and zwitterionic surfactants, as desired.

The extraction reagent of the invention may also contain other preservatives, buffering agents and the like, so long as the intended effect of the invention is not impaired. The extraction reagent of the invention may be housed with all of the constituent components mixed in a single container, or it may be separated into two or more components and housed in separate containers, and mixed together at the time of use.

[Embodiment 4: Immunoassay Kit for Detection of *Staphylococcus aureus* Antigen]

The immunoassay kit for detection of *Staphylococcus aureus* according to this embodiment is an immunoassay kit for detection of *Staphylococcus aureus* comprising the aforementioned reagent for extraction of *Staphylococcus aureus* antigen. With such a kit it is possible to more reliably assess whether a test strain is MRSA or MSSA, based on results of detection of antigen in the obtained extract. The immunoassay kit for detection of *Staphylococcus aureus* according to this embodiment may comprise, as necessary, a container which houses the extraction reagent, detection means for the antigen, a measurement method manual, and if necessary standard products for the analytes (antigens). For example, an immunoassay kit for detection of *Staphylococcus aureus* comprising antigen immunoassay means as the antigen detection means is a preferred example of an immunoassay kit according to this embodiment.

EXAMPLES

The present invention will now be explained in greater detail by examples, with the understanding that the technical scope of the invention is under no restriction from the following description. Unless otherwise specified, the "%" and "part" values throughout the examples refer to wt % and parts by weight.

Example 1

Preparation of *Staphylococcus* Antigen Extraction Reagent and Extraction of *Staphylococcus aureus* Antigen from MRSA 1. Preparation of MRSA Specimen After dissolving 17 g of Brain Heart Broth (Catalog No.: 110493, Merck) in 100 ml of water, the mixture was subjected to autoclave sterilization at 121° C. for 20 minutes to prepare a culture medium. A clinically isolated MRSA strain was seeded in the medium and cultured at 37° C. for 48 hours. Upon completion of the culturing, the cells were collected by centrifugal separation and lysed in 10 ml of 20 mM phosphate buffer (pH 7.2). Next, the lysed MRSA cell solution (50 µl) was dispensed into a microtube and the supernatant was removed by centrifugal separation.

2. Antigen Extraction from MRSA using *Staphylococcus aureus* Antigen Extraction Reagent A *Staphylococcus* antigen extraction reagent comprising 0.1 M HCl and a *Staphylococcus* antigen extraction reagent comprising 0.1 M HCl and different 2.0% (w/w) surfactants (both with pH of no higher than 5.0) were prepared. The surfactants used were the anionic surfactant EMAL NC35 (product of Kao Corp.), the nonionic surfactants MEGA-8 (product of Dojindo), TritonX-100 (product of Wako Pure Chemical Industries, Ltd.), Tween20 (product of Wako Pure Chemical Industries, Ltd.) and Brij721 (product of Sigma), the cationic surfactant QUARTAMIN 86W (product of Kao Corp.), and the zwitterionic surfactants CHAPS (product of Dojindo) and AMPHITOL 20N (product of Kao Corp.).

To the supernatant-removed MRSA cells described in 1. above there were added each of the aforementioned extraction reagents, and as a control, a 0.1 M sodium hydroxide solution or 0.1 M nitrous acid solution (200 µl), to prepare cell suspensions. Each cell suspension was boiled for 2 minutes in boiling water for extraction. After cooling the extracted cell suspension on ice, 0.1 M NaOH (200 µl) and 100 mM phosphate buffer (pH 8.0, 20 µl) were added to the cell suspension for neutralization to pH 6.0-8.0. Next, centrifugal separation was performed at 1,500×g for 5 minutes and the supernatant was obtained to prepare a specimen for subsequent immune antibody measurement.

3. Preparation and Solid Phasing of Anti-PBP2 Antibody and Anti-PBP2' Antibody

Antibodies for specific detection of PBP2 and PBP2' (anti-PBP2 antibody and anti-PBP2' antibody) were prepared according to a common method (for example, the method described in Japanese Patent Publication No 3638731). A known screening method was used to find a combination of an "antibody for solid phase" and a "labeling antibody" among the obtained monoclonal antibodies, suitable for use in sandwich ELISA. Biotin was bonded to the labeling antibody by chemical modification using a known method (based on the method described in P. Tijssen: Enzyme Immunoassay, Tokyo Kagaku Dojin, pp. 216-241).

The anti-PBP2 antibody and anti-PBP2' antibody "for solid phase" were diluted to a concentration of 2 µg/ml using 0.1 M PBS (pH 7.5), and dispensed into a plate at 50 µl per well and reacted at 25° C. for 1 hour for solid-phasing of the antibody, Next, a 50 mM Tris-HCl buffering solution (pH 7.2) (TBS-T) containing 0.05% Tween20 and 150 mM sodium chloride was used 3 times at 200 µl per well for rinsing. A TBS buffering solution (pH 7.0) containing 2% BSA was then added at 200 µl per well and reacted for 1 hour for blocking. Rinsing was then performed 3 times with TBS-T.

4. Immunoassay Using Solid-Phased Anti-PBP2 Antibody and Anti-PBP2' Antibody

A specimen diluted 10-fold with a diluent (1% BSA TBS-Tween 0.1%) was dispensed into a microplate with solid-phased antibody at 50 µl per well, and antigen-antibody reaction was conducted at 25° C. for 1 hour. Rinsing was then performed 3 times with TBS-T (Tween20 concentration: 0.1%) at 200 µl per well. Next, biotin-bonded labeling anti-PBP2 antibody and anti-PBP2' antibody were diluted to 1.0 µg/ml with a diluent (1% BSA TBS-Tween 0.1%) and dispensed into the plate at 50 µl per well, for antigen-antibody reaction at 25° C. for 1 hour.

After rinsing 3 times with TBS-T (Tween20 concentration: 0.1%) at 200 µl per well, streptavidin-bound peroxidase (Catalog No.: 21126 by Thermo) prepared to 1 µg/ml with a diluent (1% BSA TBS-Tween 0.1%) was dispensed into the plate at 50 µl per well, and reacted at 25° C. for 30 minutes.

After rinsing 3 times with TBS-T (Tween20 concentration: 0.1%) at 200 µl per well, 25 mM citrate buffer (pH 5.0) containing 1 mg/ml of o-phenylenediamine and 0.5 µl/ml of hydrogen peroxide was added at 100 µl per well for coloring reaction for 10 minutes, after which a concentrated sulfuric acid solution diluted 90-fold with purified water was added at 30 µl per well to terminate the reaction. A microplate reader (SPECTRAmax by Molecular Devices) was used to measure the absorbance at a wavelength of 490 nm. The results are shown in Table 1.

(Results and Discussion)

The results of measurement using antibodies for PBP2' and PBP2 are shown in the table as the values after subtracting the absorbance measured using a diluent (TBS-T) instead of a specimen, as a blank. As shown in Table 1, for a specimen extracted using the hydrochloric acid-containing extraction reagent or the hydrochloric acid- and surfactant-containing extraction reagent, the measured values for both PBP2' and PBP2 were clearly higher than the blank, and both PBP2' and PBP2 could be detected. It was also confirmed that a difference in extraction efficiency is seen depending on the type of surfactant, and particularly high absorbance was obtained when QUARTAMIN 86W, AMPHITOL 20N or Brij721 was used in combination with hydrochloric acid. Similar results were also obtained when using other acids (acetic acid, citric acid, phosphoric acid, sulfuric acid and nitric acid) instead of hydrochloric acid.

On the other hand, when a basic extraction reagent employing sodium hydroxide was used, detection of PBP2' was possible, but the absorbance with measurement of PBP2 was 0 and detection of PBP2 was not possible. This suggests that under basic conditions, PBP2 is not satisfactorily extracted by sodium hydroxide, or if it is extracted the PBP2 later decomposes in the extract, making it undetectable as a measured value. In the method using nitrous acid, neither PBP2 nor PBP2' could be detected. While the reason for this is not clear, it is conjectured that an antigen extraction method with nitrous acid such as disclosed in Non-patent document 5 was used for the purpose of extracting carbohydrate antigens such as sugar chains, while no effect was obtained for the purpose of extracting protein antigens such as PBP2 and PBP2'.

TABLE 1

| Extraction reagent | Absorbance ($\Delta OD_{490\,nm}$) | |
|---|---|---|
| | PBP2' | PBP2 |
| 0.1M HCl/2% EMAL NC35 | 0.046 | 0.095 |
| 0.1M HCl/2% MEGA-8 | 0.024 | 0.049 |
| 0.1M HCl/2% TritonX-100 | 0.043 | 0.052 |
| 0.1M HCl/2% Tween20 | 0.057 | 0.048 |
| 0.1M HCl/2% Brij721 | 0.161 | 0.132 |
| 0.1M HCl/2% QUARTAMIN 86W | 0.362 | 0.160 |
| 0.1M HCl/2% CHAPS | 0.048 | 0.068 |
| 0.1M HCl/2% AMPHITOL 20N | 0.145 | 0.176 |
| 0.1M HCl | 0.025 | 0.043 |
| 0.1M NaOH | 0.080 | 0.000 |
| 0.1M HNO$_2$ | 0.000 | 0.000 |

Example 2

Detection of MRSA by Western Blotting

Following the method described in Example 1, antigen was extracted from a clinically isolated strain of MRSA, and was electrophoresed according to the method of Shagger et al. Purified antigen was simultaneously electrophoresed as a standard sample. Following the electrophoresis, the electrophoresed extracted antigen was immobilized on a PVDF membrane according to the method of Towbin et al. (Towbin et al, Proc. Natl, Acad, Sci. USA, vol. 76, p. 4350-4354 (1979)). Next, the portion without the protein being immobilized on the PVDF membrane was blocked with TBS buffering solution containing 2% BSA.

On the blocked PVDF membrane there was dropped polyclonal antibody for PBP2' or PBP2, diluted 1,000-fold with 1% BSA TBS-Tween 0.1%, and the membrane was allowed to stand at room temperature for 1 hour. The PVDF membrane was then rinsed with TBS-T (Tween20 concentration: 0.1%) to remove the unreacted polyclonal antibody. Next, peroxidase-labeled anti-mouse IgG antibody (commercial product) diluted 5,000-fold with 0.1% BSA (TBS-Tween 0.1%) was dropped thereon and the membrane was allowed to stand at room temperature for 30 minutes. The PVDF membrane was then rinsed again with TBS-T (Tween20 concentration: 0.1%), and subsequently the PVDF membrane was rinsed with purified water. After dropping 4 ml of an ECL-PLUS luminescence detection kit (Catalog No.: RPN2132, product of GE), an LAS-3000 luminescence detector (product of Fuji-Film Corp.) was used to detect the band accumulated over 6 minutes. The band was detected near 81 kDa for PBP2 and near 78 kDa for PBP2'.

(Results and Discussion)

The results are shown in Table 2. Samples with a confirmed band were indicated by "+", and those without were indicated by "−". As shown in Table 2, this extraction method allowed simultaneous extraction of both PBP2 and PBP2'.

When abasic extraction reagent employing sodium hydroxide was used, a band could be detected for PBP2', but no band could be confirmed for PBP2, similar to the results of Example 1. In the method using nitrous acid, neither PBP2 nor PBP2' could be detected.

TABLE 2

| Extraction reagent | Confirmation of bands | |
| --- | --- | --- |
|  | PBP2' | PBP2 |
| 0.1M HCl/2% EMAL NC35 | + | + |
| 0.1M HCl/2% MEGA-8 | + | + |
| 0.1M HCl/2% TritonX-100 | + | + |
| 0.1M HCl/2% Tween20 | + | + |
| 0.1M HCl/2% Brij721 | + | + |
| 0.1M HCl/2% QUARTAMIN 86W | + | + |
| 0.1M HCl/2% CHAPS | + | + |
| 0.1M HCl/2% AMPHITOL 20N | + | + |
| 0.1M HCl | + | + |
| 0.1M NaOH | + | − |
| 0.1M HNO$_2$ | − | − |

Example 3

Discrimination of MRSA and MSSA Using Method for Assessing *Staphylococcus aureus* According to the Invention In order to confirm that MRSA and MSSA can be discriminated by the method for assessing *Staphylococcus aureus* according to the invention, 3 strains each that were clinically isolated strains previously confirmed as MRSA or MSSA were used in a discrimination test for MRSA and MSSA. Each strain was cultured by the same method as in Example 1, and the collected cells were suspended in 200 μl of a 0.1 M HCl±2.0% Tween20 solution (pH≤5.0), as the extraction reagent. The cell suspension was boiled for 2 minutes in boiling water and cooled on ice, and then 0.1 M NaOH (200 μl) and 100 mM phosphate buffer (pH 8.0, 20 μl) were added to the cell suspension for neutralization to pH 6.0-8.0. This was followed by centrifugation at 1,500×g for 5 minutes, and the supernatant was used as specimen and supplied for the immunoassay method described in 4. of Example 1.

(Results and Discussion)

The results are shown in Table 3. In the results, specimens with clearly higher absorbance than the blank are shown as "+", and specimens with no increase in absorbance are shown as "−", As seen in Table 3, all 3 MRSA strains possessed both PBP2 and PBP2', with both antigens actually being detected, allowing their confirmation as MRSA. On the other hand, the MSSA strains did not possess PBP2', with only PBP2 being detected.

These results demonstrated that this extraction method is effective for discriminating MRSA and MSSA.

TABLE 3

|  |  | Detected antigen | |
| --- | --- | --- | --- |
|  |  | PBP2 | PBP2' |
| MRSA | Strain 1 | + | + |
|  | Strain 2 | + | + |
|  | Strain 3 | + | + |

TABLE 3-continued

|  |  | Detected antigen | |
| --- | --- | --- | --- |
|  |  | PBP2 | PBP2' |
| MSSA | Strain 1 | + | − |
|  | Strain 2 | + | − |
|  | Strain 3 | + | − |

Example 4

Discrimination of MRSA and MSSA by Antibody Array Method

In order to confirm that MRSA and MSSA can be discriminated by the method for assessing *Staphylococcus aureus* according to the invention, 29 strains each of clinically isolated MRSA and MSSA strains, previously confirmed as MRSA or MSSA, were used in a discrimination test for MRSA by an antibody array method. Each strain was cultured by the same method as in Example 1, and the collected cells were suspended in 200 μl of a 0.1 M HCl+2.0% AMPIIITOL 20N solution (pH≤5.0), as the extraction reagent. The cell suspension was boiled for 2 minutes in boiling water and cooled on ice, and then 0.1 M NaOH (200 μl) and 100 mM phosphate buffer (pH 8.0. 20 μl) were added to the cell suspension for neutralization to pH 6.0-8.0. Next, centrifugal separation was performed at 1,500×g for 5 minutes andtheaupornaiumtvvox used as a specimen.

Preparation of Antibody Array

An antibody array with the layout shown in FIG. 1 was prepared. The array slide used was a PATH Slide (Gentel Biosciences), and the anti-PBP2 antibody and anti-PBP2' antibody for solid phase used in Example 1 were spotted on the slide using a microinject spotter, at a concentration of 0.5 mg/ml each. As a positive control, biotinylated BSA was spotted at a concentration of 1.0 μg/ml. Each prepared slide was allowed to stand at room temperature ford hours, and then stored at 4° C. prior to use.

Using a 16-well slide incubation chamber (No. 10486046 by GE Healthcare) and a Chip Clip (No. 10486081 by GE Healthcare), the periphery of the array was divided by an enclosing block. A TBS buffering solution (pH 8.0) containing 2% BSA was added to each well at 100 μl per well and reacted for 1 hour for blocking. Next, 100 μl of TBS-T was added to each well for rinsing, and this procedure was repeated 3 times. The sample extracted from the strain was then dispensed into the wells at 50 μl per well, and antigen-antibody reaction was conducted at 25° C. for 1 hour, Rinsing was then perfoimed 3 times with TBS-T (Tween20 concentration: 0.1%) at 100 μl per well. Next, a mixture of biotin-bonded labeling PBP2 antibody and PBP2' antibody prepared to a concentration of 10.0 μg/ml each with a diluent (1% BSA TBS-Tween 0.1%) was dispensed at 50 μl per well, for antigen-antibody reaction at 25° C. for 1 hour.

After rinsing 3 times with TBS-T at 100 μl per well, a biotinylated luciferase-streptavidin complex, of InteliteAB (product of Kikkoman Corp.) was dispensed at 50 μl per well and reacted for 30 minutes. The plate was then rinsed 3 times with TBS-T at 100 μl per well. and further rinsed once with TBS at 100 μl per well.

For measurement of the antibody array there was used an LAS300 Lumino Image Analyzer (product of FujiFilm), as a luminescence detector. The InteliteAB luciferase luminescent substrate solution containing luciferin, ATP and magnesium ion was added at 100 μl per well to produce luminescence. and the luminescence was measured for 5 minutes.

(Results and Discussion)

Figure 2:
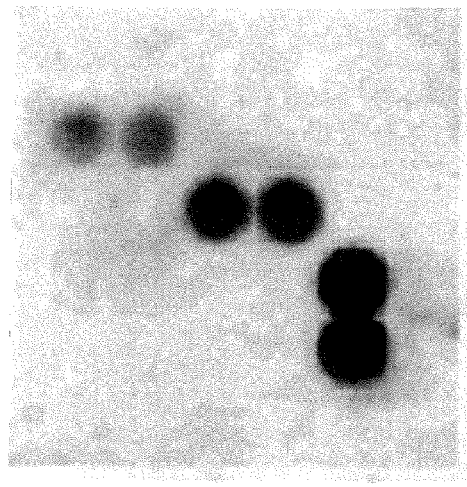
FIG. 2 shows measurement images for obtained MSSA and MRSA antibody arrays.
Figure 2:
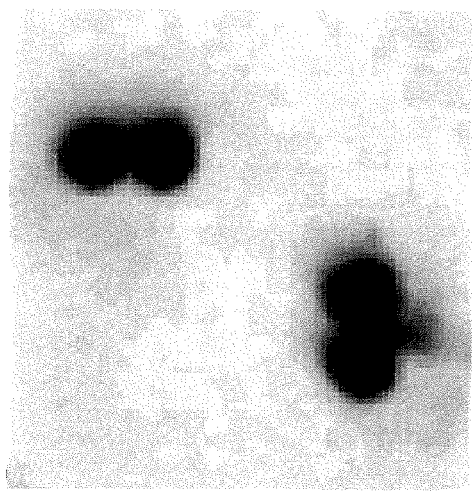

FIG. 2 shows antibody array measurement images for the obtained MSSA and MRSA. The sections with detected luminescence appear black in the images. When MSSA was measured, the sections where anti-PBP2 antibody was spotted emitted luminescence, indicating detection of PBP2. The sections where anti-PBP2' antibody was spotted did not emit luminescence, indicating that PBP2' was not in the specimen. The specimen could therefore be identified as MSSA. When MRSA was measured, the sections where PBP2 and PBP2' antibody were spotted both emitted luminescence, indicating that PBP2 and PBP2' were present in the specimen. The specimen could therefore be identified as MRSA.

Table 4 shows the results of discriminating 29 strains each of MRSA and MSSA, upon measurement with an antibody array. The results are shown as the number of specimens in which each antigen was detected, with respect to the number of tests. For antigen detection, detection was defined as measurement of a luminescence amount of at least 10 times higher than that of a blank at the location of the solid-phased antibody. As seen in Table 4, both PBP2 and PBP2' antigens were simultaneously detected in all 29 MRSA strains, allowing their confirmation as MRSA. On the other hand, the MSSA strains did not possess PBP2', with only PBP2 being detected.

These results demonstrated that the assessment method of the invention is effective for discriminating MRSA and MSSA.

TABLE 4

|  |  | Detected antigen | |
|---|---|---|---|
|  |  | PBP2 | PBP2' |
| MRSA | Number detected | 29 | 29 |
|  | Number tested | 29 | 29 |
| MSSA | Number detected | 29 | 0 |
|  | Number tested | 29 | 29 |

Example 5

Discrimination of MRSA and MSSA by Immunochromatography Method

In order to confirm that MRSA and MSSA can be discriminated by the test method of the invention, 29 strains of MRSA and 29 strains of MSSA, clinically isolated and previously confirmed as MRSA or MSSA, were used in a discrimination test for MRSA by an immunochromatography method. The immunochromatography test strips were prepared by a common method, as described below.

The labeling anti-PBP2 antibody and anti-PBP2' antibody used in Example 1 were each labeled with gold colloid, and atomized on a polystyrene nonwoven fabric. This was designated as the labeled reagent site. Separately, the anti-PBP2 antibody for solid phase and anti-PBP2' antibody for solid phase used in Example 1 were each coated onto the same nitrocellulose membrane to create two test lines, and were thoroughly dried. As a control reagent, Anti-Mouse IgG was coated in the same manner on a nitrocellulose membrane and thoroughly dried. This was designated as the capture reagent site.

The two prepared sites were combined with a glass filter for supply of specimen and absorbing filter paper, to form an immunochromatography test strip.

In the same manner as Example 4, antigen was extracted from 29 MRSA strains and 29 MSSA strains, for use as measuring samples. A 100 µl portion of measuring sample was loaded at the specimen supply site of the prepared immunochromatography test strip, and after 15 minutes, the test lines at the capture reagent section were visually confirmed.

(Results and Discussion)

MSSA was confirmed to have coloring only at the PBP2 detection test line. On the other hand, MRSA was confirmed to have coloring lines for both the PBP2 detection test line and the PBP2' detection test line. The number of measured tests and detections are shown in Table 5. These results demonstrated that the assessment method of the invention is effective for discriminating MRSA and MSSA.

TABLE 5

|  |  | Detected antigen | |
|---|---|---|---|
|  |  | PBP2 | PBP2' |
| MRSA | Number detected | 29 | 29 |
|  | Number tested | 29 | 29 |
| MSSA | Number detected | 29 | 0 |
|  | Number tested | 29 | 29 |

The present invention has been explained above by examples. However, these examples are merely illustrative and may incorporate various modifications, and it will be appreciated by a person skilled in the art that such modifications are within the scope of the invention.

Industrial Applicability

As explained above, the present invention allows early detection of MRSA and permits appropriate measures to be taken for MRSA-infected patients or MRSA-infected areas, and when *Staphylococcus aureus* has been detected, it allows reliable distinction of whether the strain is MRSA, or MSSA which must be handled differently than MRSA, so that appropriate measures may be taken for each, and it is therefore highly useful for examination and diagnosis, and especially routine examination and diagnosis, of *Staphylococcus aureus*.

The invention claimed is:

1. A method for extracting a *Staphylococcus aureus* antigen which comprises: contacting an extraction reagent with a pH of no higher than 5.0, containing one or more acids selected from among hydrochloric acid, acetic acid, citric acid, phosphoric acid, sulfuric acid and nitric acid with *Staphylococcus aureus* in a specimen, to extract a *Staphylococcus aureus* antigen comprising a methicillin-resistant *Staphylococcus aureus* antigen and/or a methicillin-sensitive *Staphylococcus aureus* antigen, from the *Staphylococcus aureus* in a specimen, wherein the methicillin-resistant *Staphylococcus aureus* antigen is penicillin-binding protein 2' and the methicillin-sensitive *Staphylococcus aureus* antigen is penicillin-binding protein 2, and wherein, when the *Staphylococcus aureus* is a methicillin-resistant Staphylococcus aureus, then both the penicillin-binding protein 2' and the penicillin binding protein 2 are extracted, and when the *Staphylococcus aureus* is a methicillin-sensitive *Staphylococcus aureus*, then the penicillin-binding protein 2 is extracted, while the penicillin-binding protein 2' is not extracted, wherein the extraction reagent contains one or more surfactants selected from the group consisting of an anionic surfactant, zwitterionic surfactant, cationic surfactant and nonionic surfactant.

2. The method for extracting a *Staphylococcus aureus* antigen according to claim 1, wherein the surfactant is one or more surfactants selected from the group consisting of sodium polyoxyethylene nonylphenyl ether sulfate, octanoyl-N-methyl-qlucamine, polyoxyethylene octylphenyl ether, polyoxyethylene(20)sorbitan monolaurate, polyoxyethylene alkyl ether, polyoxyethylene tridecyl ether, polyoxyethylene(20)sorbitan monooleate, polyoxyethylene(21)stearyl ether, stearyltrimethylammonium chloride, lauryltrimethylammonium chloride, 3-(3-cholamidepropyl)dimethylammonio-1-propanesulphonate, 3-[(3-cholamidepropyl)dimethylammonio]-2-hydroxypropanesulfonate, lauryltrimethylamine oxide and lauryltrimethylamino carboxy betaine.

3. The method for extracting a *Staphylococcus aureus* antigen according to claim 1, wherein the antigen extraction is carried out at a temperature of 25 to 100° C.

4. The method for extracting a *Staphylococcus aureus* antigen according to claim 2, wherein the antigen extraction is carried out at a temperature of 25 to 100 ° C.

* * * * *